(12) United States Patent
McNeely et al.

(10) Patent No.: US 6,601,613 B2
(45) Date of Patent: Aug. 5, 2003

(54) FLUID CIRCUIT COMPONENTS BASED UPON PASSIVE FLUID DYNAMICS

(75) Inventors: Michael R. McNeely, Salt Lake City, UT (US); Arnold R. Oliphant, Erda, UT (US); Mark K. Spute, Salt Lake City, UT (US)

(73) Assignee: BioMicro Systems, Inc., Salt Lake City, UT (US)

( * ) Notice: Subject to any disclaimer, the term of this patent is extended or adjusted under 35 U.S.C. 154(b) by 0 days.

(21) Appl. No.: 09/967,402

(22) Filed: Sep. 27, 2001

(65) Prior Publication Data

US 2002/0036018 A1 Mar. 28, 2002

Related U.S. Application Data

(63) Continuation of application No. 09/417,691, filed on Oct. 31, 1999, now Pat. No. 6,296,020.
(60) Provisional application No. 60/138,092, filed on Jun. 8, 1999, and provisional application No. 60/103,970, filed on Oct. 13, 1998.

(51) Int. Cl.[7] .................................................. G05D 7/00
(52) U.S. Cl. ....................... 137/833; 137/806; 137/841; 251/368; 204/601
(58) Field of Search ................................ 137/806, 833, 137/841; 204/601; 251/368

(56) References Cited

U.S. PATENT DOCUMENTS

| | | | |
|---|---|---|---|
| 3,191,623 A | 6/1965 | Bowles | 137/833 |
| 3,327,726 A | 6/1967 | Hatch, Jr. | 137/806 |
| 3,417,770 A | 12/1968 | Denlson | 137/806 |
| 3,799,742 A | 3/1974 | Coleman | |
| 3,993,062 A | 11/1976 | Jess | 128/214 |

(List continued on next page.)

FOREIGN PATENT DOCUMENTS

| | | |
|---|---|---|
| EP | 0933126 A1 | 8/1999 |
| EP | 1016864 A2 | 7/2000 |
| WO | WO 97/02357 | 1/1997 |
| WO | WO 98/29736 | 7/1998 |
| WO | WO 98/56505 | 12/1998 |
| WO | WO 99/56954 | 11/1999 |
| WO | WO 99/64836 | 12/1999 |
| WO | 00/21659 | 4/2000 |
| WO | 01/41931 | 6/2001 |
| WO | 01/88525 | 11/2001 |
| WO | 01/90614 | 11/2001 |

OTHER PUBLICATIONS

Banerjee, "Structured custom design for LOC applications.," ASME Microfluidics for Lab–on–Chip (LOC) Pre–Seminar Workshop, Sep. 9, 2001.

(List continued on next page.)

Primary Examiner—A. Michael Chambers
(74) Attorney, Agent, or Firm—Madson & Metcalf (57) ABSTRACT

Methods of controlling fluid flow through microchannels by use of passive valves or stopping means in the microchannels is presented. The passive valves act as pressure barriers impeding flow of solution past the stopping means until enough force is built up to overcome the force of the pressure barrier. Well planned use of such stopping means acting as passive valves allows the flow of fluids through microchannels to be regulated so as to allow fluids to be mixed or diluted after being introduced via a single channel, or to be split into multiple channels without the need for individual pipetting. Flow through the multiple channels can be regulated to allow a series of sister wells or chambers to all fill prior to the fluid flowing beyond any one of the sister wells or chambers. The filling of sister wells or chambers in this manner allows all wells or chambers to undergo reactions in unison. The use of air ducts to prevent trapping of air in the microchannels is also presented.

40 Claims, 9 Drawing Sheets

U.S. PATENT DOCUMENTS

| | | |
|---|---|---|
| 4,426,451 A | 1/1984 | Columbus |
| 4,618,476 A | 10/1986 | Columbus .................... 422/100 |
| 4,676,274 A * | 6/1987 | Brown ........................ 137/806 |
| 4,756,884 A | 7/1988 | Hillman et al. ................ 422/73 |
| 4,868,129 A | 9/1989 | Gibbons et al. |
| 4,946,795 A | 8/1990 | Gibbons et al. |
| 4,963,498 A | 10/1990 | Hillman et al. ................ 436/69 |
| 5,051,182 A | 9/1991 | Wang et al. ........... 210/500.27 |
| 5,077,017 A | 12/1991 | Gorin et al. |
| 5,104,813 A | 4/1992 | Besemer et al. ............ 436/179 |
| 5,119,116 A | 6/1992 | Yu .............................. 346/140 |
| 5,223,219 A | 6/1993 | Subramanian et al. ......... 422/55 |
| 5,230,866 A | 7/1993 | Shartle et al. ............... 422/100 |
| 5,304,487 A | 4/1994 | Wilding et al. .............. 435/291 |
| 5,378,504 A | 1/1995 | Bayard et al. ................ 426/377 |
| 5,427,946 A | 6/1995 | Kricka et al. ................ 435/291 |
| 5,486,335 A | 1/1996 | Wilding et al. ................ 422/55 |
| 5,498,392 A | 3/1996 | Wilding et al. ............ 422/68.1 |
| 5,587,128 A | 12/1996 | Wilding et al. ................ 422/50 |
| 5,635,358 A | 6/1997 | Wilding et al. ............... 435/7.2 |
| 5,637,469 A | 6/1997 | Wilding et al. ............ 435/7.21 |
| 5,726,026 A | 3/1998 | Wilding et al. ............ 435/7.21 |
| 5,726,404 A | 3/1998 | Brody ...................... 200/81 R |
| 5,730,187 A | 3/1998 | Howitz et al. .............. 137/833 |
| 5,846,396 A | 12/1998 | Zanzuchhi et al. .......... 204/601 |
| 5,856,174 A | 1/1999 | Lipshutz et al. ......... 435/286.5 |
| 5,866,345 A | 2/1999 | Wilding et al. ............ 435/7.21 |
| 5,869,004 A | 2/1999 | Parce et al. ................. 422/100 |
| 5,900,130 A | 5/1999 | Benvegnu et al. .......... 204/453 |
| 5,910,287 A | 6/1999 | Cassin et al. |
| 5,922,591 A | 7/1999 | Anderson et al. ........... 435/287 |
| 5,922,604 A | 7/1999 | Stapleton et al. ............. 436/46 |
| 5,928,880 A | 7/1999 | Wilding et al. ............ 435/7.21 |
| 5,955,029 A | 9/1999 | Wilding et al. ............ 422/68.1 |
| 5,958,344 A | 9/1999 | Levine et al. ................ 422/103 |
| 5,976,336 A | 11/1999 | Dubrow et al. ............. 204/453 |
| 5,980,719 A | 11/1999 | Cherukuri et al. .......... 204/600 |
| 5,992,820 A | 11/1999 | Fare et al. ............. 251/129.01 |
| 6,004,515 A | 12/1999 | Parce et al. .................. 422/100 |
| 6,043,080 A | 3/2000 | Lipshutz et al. ......... 435/287.2 |
| 6,046,056 A | 4/2000 | Parce et al. .................. 436/514 |
| 6,048,498 A | 4/2000 | Kennedy ....................... 422/99 |
| 6,068,752 A | 5/2000 | Dubrow et al. ............. 204/604 |
| 6,086,740 A | 7/2000 | Kennedy ..................... 204/601 |
| 6,086,825 A | 7/2000 | Sundberg et al. ........... 422/100 |
| 6,193,471 B1 | 2/2001 | Paul ............................ 417/53 |
| 6,296,020 B1 | 10/2001 | McNeely et al. ........... 137/806 |

OTHER PUBLICATIONS

Zeng, Jun, et al., "Design Analyses of Capillary Burst Valves in Centrifugal Microfluidics," Technical Proceeding of mTAS (Micro analysis systems) May 2000 conference, Ensched, The Netherlands, pp. 493–496.

Man, P.F., et al., "Microfabricated Capillarity–Driven Stop Valve and Sample Injector." University of Michigan.

Anderson, Rolfe C. et al., "Advances in Integrated Genetic Analysis," Affymetrix, Inc.

"Recent Patent in Microfabricatin and Microfluidics", Nature Biotechnology, vol. 17, Jun. 1999, p. 606.

Anderson, R. C. et al., "Microfluidic Biochemical Analysis System," Int. Cong. On Solid–State Sens. and Act Transducers, 1997, Chicago, Jun. 16–19, 1997, 477–480.

Brahmasandra, S.N. et al., "A Microfabricated Fluidic Reaction and Separation System for Integrated DNA Analysis," Micro Total Analysis Systems, 1998, D.J. Harrison and A Van Den Berg. Eds Kluwer Acad Publ. Dordrecht (1998) Proceedings of the μTAS 1998 Workshop, Banff, Canada, Oct. 13–16, 1998, 307–310 and cover page.

Lee, L.P. et al., "Key ELements of Transparent Teflon Microfludic System," Micro Total Analysis System 1998, D.J. Harrison and A Van den Berg, eds. Kluwer Acad. Publ. Dordrecht (1998); Proceedings of the μTAS 1998 Workshop, Banff,Canada, Oct. 13–16, 1998, 245–48, cover page.

* cited by examiner

FLUID CIRCUIT COMPONENTS BASED UPON PASSIVE FLUID DYNAMICS

CROSS-REFERENCE TO RELATED APPLICATIONS

The present application claims the benefit of U.S. provisional patent application Ser. No. 60/103,970, filed Oct. 13, 1998, and to U.S. provisional application Ser. No. 60/138,092, filed Jun. 8, 1999, and this application is a continuation of U.S. utility application Ser. No. 09/417,691, filed Oct. 13, 1999, now U.S. Pat No. 6,296,020 issued Oct. 2, 2001, both of which are incorporated herein by reference.

BACKGROUND OF THE INVENTION

The movement of fluids through channels on a micro scale has important implications in a number of technologies. For example, in the field of molecular biology, polymerise chain reactions (PCR) have been performed in a chip containing microfabricated flow channels (U.S. Pat. Nos. 5,498,392; 5,587,128; 5,726,026). In the electronics field, thermal ink jet printers use printheads with microchannels through which ink must flow in a well controlled manner (U.S. Pat. No. 5,119,116). Proper control of fluids through microchannels has been a challenge, with microdimensions imparting difficulties not encountered at larger scales.

The publications and other materials used herein to illuminate the background of the invention or provide additional details respecting the practice, are incorporated by reference, and for convenience are respectively grouped in the appended List of References.

Surface effects describe the character of a surface on a micro scale. Materials often have unbound electrons, exposed polar molecules, or other molecular level features that generate a surface charge or reactivity characteristic. Due to scaling these surface effects or surface forces are substantially more pronounced in micro structures than they are in traditionally sized devices. This is particularly true in micro scale fluid handling systems where the dynamics of fluid movement are governed by external pressures and by attractions between liquids and the materials they are flowing through. This fact can be utilized to fabricate unique structures that function due to these surface forces.

This invention deals with the passive control of fluids within a microfluidic circuit. The passive control is generated by using the natural forces that exist on a micro scale, specifically capillarity, which is caused by the attraction or repulsion of a fluid toward certain materials. The purpose is to stop fluid flow along one path in a circuit until enough pressure is generated to push the fluid past the stopping means, or until the stopping means itself is removed or made insignificant. The pressure that is generated because of the stopping means can be utilized to move fluid through the circuit in some creative manner, or to hold fluid at a specific location.

Capillarity is usually represented by the equation $h=2\sigma_{gl}\cos(\theta_c)/gr\rho$ which describes the height (or depth), h, of a fluid within a capillary tube compared to the level of the fluid outside the capillary tube. $\theta_c$, or the contact angle of the fluid with the capillary tube material, governs whether the fluid in the tube is above or below the level of the fluid outside the tube. If the contact angle of the capillary tube material, with respect to the fluid, is less than 90°, the material is considered hydrophilic (water liking). If the contact angle of the tube material, with respect to the fluid, is greater than 90°, the material is considered hydrophobic (water fearing). $\sigma_{gl}$ represents the surface tension of the fluid with respect to the ambient (usually air) (millijoules/m²), g is the gravitational constant (m/s²), r is the radius of the capillary tube (m), and $\rho$ is the fluid density (kg/m³).

Figure 1A:
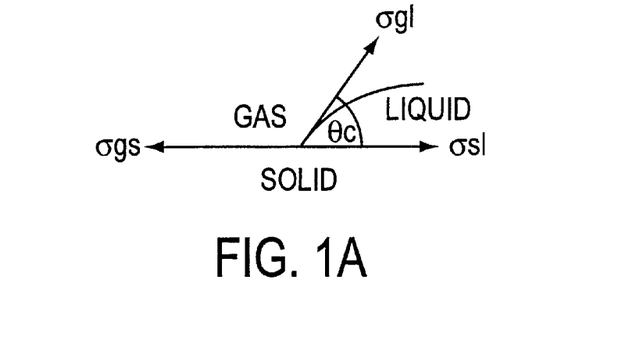
FIG. 1A shows the relation between $\sigma$ (surface tension) and $\theta_c$ (the contact angle between the meniscus of fluid and the wall of a channel).
Figure 1B:
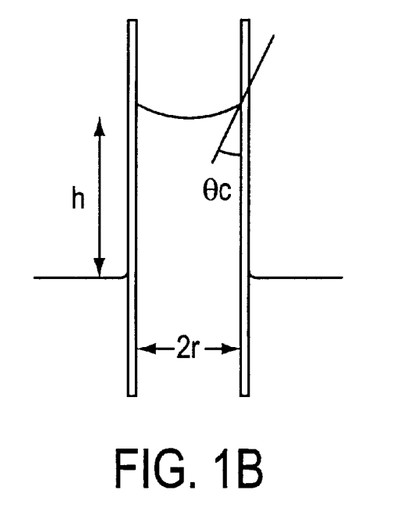
FIG. 1B illustrates the meniscus formed when hydrophilic tubing draws water into it.
Figure 1C:
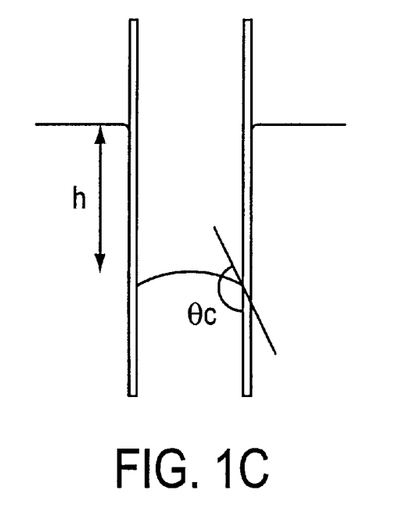
FIG. 1C illustrates the meniscus formed when a hydrophobic tubing pushes water away from the tubing.

FIGS. 1A–C illustrate the concept of hydrophilicity and hydrophobicity. FIG. 1A illustrates $\theta_c$. $\sigma_{gs}$ is the surface tension between a gas and a solid, $\sigma_{sl}$ is the surface tension between a solid and a liquid, and $\sigma_{gl}$ is the surface tension between a gas and a liquid. $\sigma_{gs}=\sigma_{sl}+\sigma_{gl}\cos(\theta_c)$. $\theta_c$ (angle in degrees) for water on various materials at around 20° C. is shown in Table 1. FIG. 1B illustrates that hydrophilic tubing, such as glass, draws water into the tube. FIG. 1C is similar to FIG. 1B but illustrates that the use of hydrophobic tubing (such as Teflon®) pushes water away from the tube.

TABLE 1

$\theta_c$ for Selected Materials

| Material | $\theta_c$ |
|---|---|
| Glass | 0 |
| Acetal | 60 |
| Polystyrene | 84 |
| HDPE (high density polyethylene) | 87.1 |
| PVDF (polyvinylidene fluoride) | 94.8 |
| PTFE (polytetrafluoroethylene) | 104 |
| FEP (fluorinated ethylenepropylene) | 111 |

The term $\rho gh$, from the equation for capillarity, is sometimes referred to as the pressure head of a fluid, P (Pa). Re-writing the capillarity equation with respect to P gives $P=2\sigma_{gl}\cos(\theta_c)/r$. In order to effect a stopping means $\sigma_{gl}$, $\theta_c$, r, or a combination of any of the three, needs to change from one side of the stopping means to the other. This will generate a pressure barrier, which causes the fluid to stop until the pressure barrier is overcome or removed. For example, if the radius of a channel were changed in order to effect a stopping means, the equation describing the pressure required to push past the stopping means would be given by $\Delta P=2\sigma_{gl}\cos(\theta_c)(1/r_1-1/r_2)$, where $r_1$ is the radius of the channel before the stopping means and $r_2$ is the radius of the channel after the stopping means. This equation is a simplification of the physical system that may be present. A true model would take into consideration the actual channel geometries and other physical/chemical characteristics.

Figure 1D:
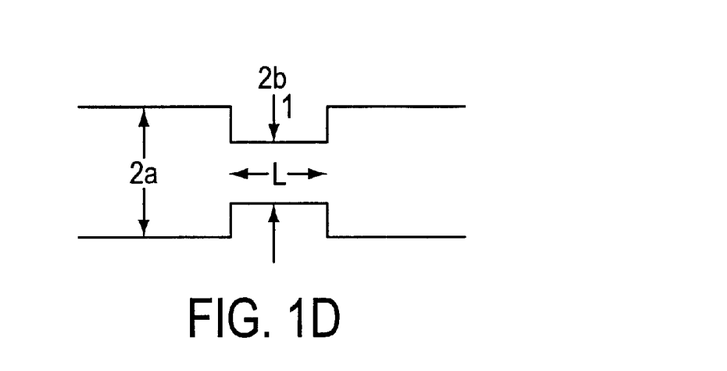
FIG. 1D illustrates a channel narrowing for passively controlling fluids in either hydrophobic or hydrophilic materials.

FIG. 1D illustrates a change in channel radius. A channel of radius a changes abruptly to a channel of a smaller radius b. The channel of radius b again changes abruptly to the larger channel of radius a. If the material were hydrophilic the stopping means would be at the point where the channel radius increases in size. In this instance $r_1$ would be given by b and $r_2$ would be given by a. This would generate a positive value for $\Delta P$, because the cosine of angles between 0 and 90 degrees (the contact angle of the material) is positive. A positive $\Delta P$ suggests a pressure barrier. If the material were hydrophobic the stopping means would be at the point where the channel decreases in size. In this case $r_1$ would be given by a, and $r_2$ by b. A negative cosine value, due to a contact angle greater than 90 degrees, would be multiplied by a negative $(1/r_1-1/r_2)$ term, resulting in a positive $\Delta P$, or a pressure barrier.

If the contact angle of the material were to change, such as a hydrophilic channel having a hydrophobic region, this can also provide a stopping means. This situation would be characterized by the equation $\Delta P=2\sigma_{gl}[\cos(\theta_{c1})-\cos(\theta_{c2})]/r$, where $\theta_{c1}$ is the contact of the material after the stopping means (hydrophobic). A negative cosine of $\theta_{c2}$ would result in a positive $\Delta P$, signifying a pressure barrier.

A change in surface tension of a fluid flowing through a microfluidic circuit, such as by lining the channel walls with absorbable salts or surfactants, could also generate a stopping means. The equation describing such a pressure barrier would be given by $\Delta P=2\cos(\theta_c)(\sigma_{gl1}-\sigma_{gl2})/r$, where $\sigma_{gl1}$ is the surface tension of a fluid before the stopping means and $\sigma_{gl2}$ is the surface tension of the fluid after the stopping means. In a hydrophobic material the surface tension would need to increase across the stopping means in order to create a pressure barrier.

This invention deals with the passive control of fluids through microfluidic channels using the stopping means described in the previous paragraphs. More specifically, the stopping means derived by reducing the radius, or cross-sectional flow area, of a flow channel containing aqueous based, or polar, fluids in a hydrophobic material, or a material coated with a hydrophobic film. Also encompassed is the control of nonpolar fluids within a hydrophilic material or a material that has been coated with a hydrophilic film. A short channel narrowing, or restriction, with these characteristics can act as a passive valve.

A variety of combinations of channel material and fluid combinations can be used to achieve the desired effect of controlling fluid flow via the use of restrictions or narrowings within microchannels to act as valves. The following are some examples of such useful combinations:

(A) PTFE (Teflon® or polytetrafluoroethylene), FEP (fluorinated ethylenepropylene), PFA (perfluoralkoxy alkane) or PVDF (polyvinylidene fluoride) as the channel material and polar solutions such as water, saline or buffer solutions not possessing a significant percentage of surfactants, this percentage being known or easily determined by one of skill in the art.

(B) Metals, glass, PMMA (polymethylmethacrylate), polycarbonate, Nylon 6/12 or PVC (polyvinylchloride) as the channel material and non-polar solutions such as hexane, heptane, toluene or benzene.

(C) PTFE, FEP, PFA of PVDF as the channel material with a hydrophilic coating such as Elastophilic™ and non-polar solutions such as those mentioned in (B).

(D) Metals, glass, PMMA, polycarbonate, Nylon 6/12 or PVC as the channel material with a hydrophobic coating such as Teflon® AF and polar solutions such as those mentioned in (A).

Valving relies upon the fact that the developing flow of a fluid stream requires extra pressure, or work, or energy, to go through a stopping means, and that it would, therefore, preferentially take a path of lesser resistance or stop altogether until enough pressure is built up that forces the fluid through the stopping means. Developing flow is defined as an advancing stream of fluid that possesses a moving interface of solution and air or some other gas. The point of interface is defined as the meniscus. Another characteristic of developing flow is that the surfaces of the flow chamber in front of, or downstream of, the advancing meniscus are not significantly wetted with the fluid that is flowing. Established flow, on the other hand, is where there is no moving meniscus and where all surfaces of the flow channels are significantly wetted.

The scope of this invention is the use of various stopping means that are designed to control the flow of fluid in a network of fluid channels. More specifically this invention details the use of short restrictions, or fluid channel narrowings, designed to control the flow of fluid in a network of hydrophobic fluid channels. The narrowness of the restriction, and its length, depend on the type and extent of fluid control that is required. Generally, however, only a short restriction is desirable so that the restriction itself does not significantly affect established flow in the channel once it becomes established.

SUMMARY OF THE INVENTION

The present invention discloses means of controlling the flow of fluids through microchannels in a manner to allow mixing or diluting of the fluids and/or separation of the fluids or a fluid into several channels for multiprocessing. It also discloses various means for consolidating or combining several samples or channels into a fewer number of samples or channels, and the use of air escape channels and stopping means to facilitate complicated fluid processing. The flow of fluid through the microchannels is primarily controlled by restrictions or narrowings purposely placed into the channels, e.g., by micromachining. These restrictions or narrowings act as valves. Unlike valves which require moving parts, the restrictions or narrowings can be static and their function does not depend upon their motion. Flow of fluid through the microchannels can also be controlled by changing the contact angle or the surface tension, e.g., by including films of salts or surfactants or by a hydrophobic patch in an otherwise hydrophilic channel.

BRIEF DESCRIPTION OF THE FIGURES

FIGS. 1A–D illustrate the concept of hydrophilicity and hydrophobicity.

FIGS. 2A–J illustrate a method of mixing two fluids together using a branching system of microchannels that join together. The channels include stopping means at points 'a' and 'b' to control the flow of fluid. Both fluids enter serially through a single common channel and are mixed subsequent to point 'b'.

FIGS. 3A–G illustrate a method of splitting a fluid into a series of daughter channels. The filling of all sister wells or chambers prior to fluid flowing beyond the wells or chambers is controlled by stopping means at the far end of each well or chamber.

FIGS. 4A–G illustrate the presence of air or a gas which can be trapped in a series of hydrophobic microchannels and the use of a vent to allow the air or gas to escape while preventing fluid through the vent.

DETAILED DESCRIPTION OF THE INVENTION

The invention is a method of using passive stopping means in microchannels to control the flow of fluids through the microchannels. A microchannel is defined herein to be a channel having a diameter of from 0.1 to 1000 microns. Advantage is taken of the surface effects between a fluid and the walls of the container holding the fluid. These surface effects come into play at the micro scale. The stopping means are designed to impede the flow of fluids under certain conditions thereby allowing control of the fluid. These stopping means act as passive valves because they regulate fluid flow but do not move.

An example of the effect of surface forces is capillarity. Capillarity, or capillary action, is demonstrated when water is drawn up into an open glass capillary tube without any outside pressure being applied. This is caused by the surface tension forces between the water and the glass surface, which pulls water into the capillary tube. The narrower the capillary tube the greater the effect of the force that pulls the water into the tube. One physical parameter that characterizes the magnitude of the capillary force is the contact angle between the water and the glass. For contact angles less than 90°, the material, e.g., glass, is considered to be hydrophilic and water is drawn up into the tube. When the material has a contact angle greater than 90° it is considered to be hydrophobic. In the hydrophobic case extra pressure is required to push water into an open tube. The narrower the tube the greater the force that is required. However, in both cases, once water has been introduced into the tube the flow rates of the water are dependent more on pressure gradients and friction and less on whether the material is hydrophobic or hydrophilic.

A stopping means is generated by altering the character of a microchannel in such a way as to generate a pressure barrier. A pressure barrier is made by creating an abrupt change in the capillary force a fluid experiences while flowing through a microchannel. An abrupt change in capillary force can be made by changing the diameter of the microchannel the fluid is flowing through, by changing the contact angle of the microchannel material, by changing the surface tension of the flowing fluid, or by a combination of these methods.

In a hydrophobic material a pressure barrier can be generated by decreasing the diameter of the flow channel. This restriction (a narrowing) should be sufficient to cause fluid to flow in alternate channels having a diameter greater than the restriction means. A narrowing of a channel can be effected by different means. For example, a channel of otherwise constant diameter can have a bump or ridge at one or more points that cause a narrowing just at those points.

Another alternative is a channel of one diameter narrowing suddenly to a channel of a smaller diameter, i.e., a wide channel narrowing to a less wide channel. The magnitude of the pressure barrier that is generated is proportional to the narrowness of the restriction compared to the narrowness of the channel prior to the restriction. A short restriction will have minimal effect on fluid flow once flow is established through the restriction. It is preferred that the restriction be 1–1000 $\mu$m long, more preferably 5–500 $\mu$m long, and most preferably 10–300 $\mu$m long.

In a hydrophilic material a pressure barrier can be generated by a channel restriction, similar to the method described for a hydrophobic material. However, in this case the fluid will not want to exit a restriction, due to the capillary forces that are holding it there. The magnitude of the pressure barrier that is generated is proportional to the narrowness of the restriction compared to the narrowness of the channel after the restriction. A short restriction will have minimal effect on fluid flow once flow is established through the restriction.

Also, in a hydrophilic material, a pressure barrier can be generated by changing the contact angle of the flow channel. Microfabrication techniques, for example, allow for the precise application of thin films of various materials that have a wide range of contact angles. The magnitude of the pressure barrier that is generated is proportional to the difference in the cosines of the contact angles of the materials comprising the stopping means.

A stopping means can also be generated by changing the surface tension of the fluid within the microchannel. This, also, could be realized by utilizing microfabrication techniques to deposit thin films of various salts or surfactants that are absorbed into the fluid. The magnitude of the pressure barrier that is generated is proportional to the difference in the surface tensions of the fluid on each side of the stopping means.

It is advantageous to use passive fluid dynamics to control the flow of fluid in micro channels or sets of micro channels. For example, if two daughter channels branch off of a main channel, a stopping means in one of the channels may encourage the fluid to flow in the channel with no stopping means. However, once the fluid has pushed past the stopping means, the stopping means, if designed properly, should have negligible effect on the established flow within the channels. In this case the stopping means acts as a passive valve.

The use of micro channels can be incorporated into a variety of techniques, e.g., splitting a sample into multiple chambers or samples or combining or mixing multiple samples together. Many variations of micro channel configurations can be designed for a particular need. The following examples illustrate some of the designs that are quite useful.

EXAMPLE 1

Use of Passive Valves in Micro Channels to Mix Samples

Figure 2A:
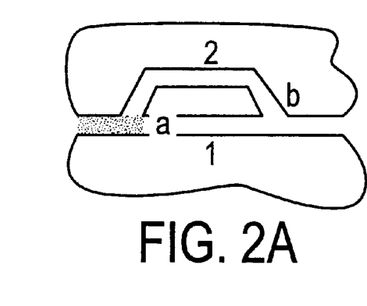
Figure 2B:
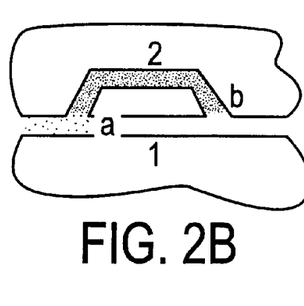
Figure 2C:
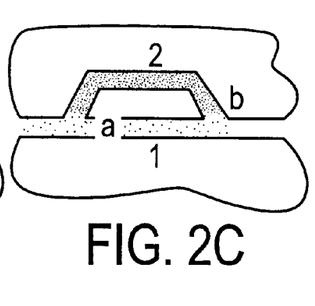
Figure 2D:
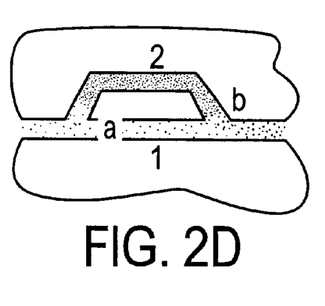

FIGS. 2A–J illustrate the use of stopping means in microchannels to regulate the flow of fluid through the channels. In FIG. 2A, fluid in the main channel encounters stopping means 'a', causing the flow to be diverted into channel 2. In FIG. 2B, the fluid in channel 2 encounters stopping means 'b' which has a greater pressure barrier than stopping means 'a'. As a result, the fluid flow is stopped by stopping means 'b' and the fluid is forced past stopping means 'a' into channel 1. FIG. 2C illustrates the fluid in channel 1 at the timepoint at which it reaches stopping means 'b'. This causes the wetting of all surfaces on all sides of stopping means 'b'. The meniscus which had been present at stopping means 'b' disappears thereby allowing fluid to freely pass stopping means 'b'. In FIG. 2D, flow proceeds in both channels 1 and 2 without obstruction. This example shown in FIGS. 2A–J shows a method by which two fluids can be mixed after insertion into a set of microchannels via a single microchannel. The example shows a first fluid inserted first into a main channel. A precisely measured amount of this first fluid can be inserted into the main channel. Following insertion of the first fluid, a second fluid is inserted into the main channel behind the first fluid. This second fluid forces the first fluid along the main channel until stopping means 'a' is reached. The first fluid is forced by this stopping means into channel 2. Once channel 2 is filled and the first fluid reaches stopping means 'b', flow through channel 2 is stopped because stopping means 'b' has a greater pressure barrier than stopping means 'a'. The force of the fluid in the main channel then forces the second fluid (all of the first fluid in this example having entered channel 2) past stopping means 'a'. When the second fluid reaches the point of stopping means 'b' the pressure barrier of stopping means 'b' is overcome due to the wetting of both sides of stopping means 'b' and the removal of the meniscus which had originally formed at this point. At this point fluid will flow through channels 1 and 2 according to their respective impedances, and the first fluid that was in channel 2 will mix with the second fluid which was in channel 1, this mixing occurring in channel 1 subsequent to stopping means 'b'.

Figure 2E:
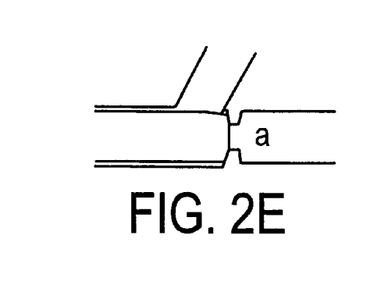
FIGS. 2E–J illustrate the structure of the stopping means and the position of fluid at the stopping means whether the stopping means is a hydrophobic restriction, hydrophilic restriction, a hydrophobic patch or a salt patch.
Figure 2F:
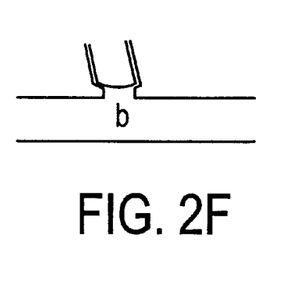
Figure 2G:
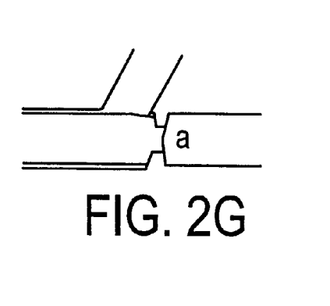
Figure 2H:
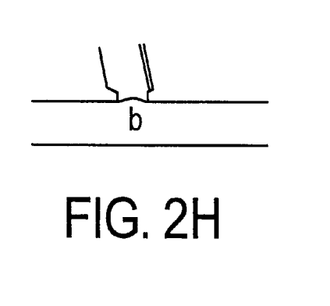
Figure 2I:
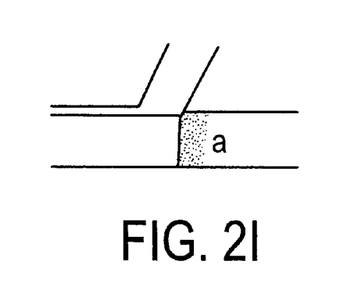
Figure 2J:
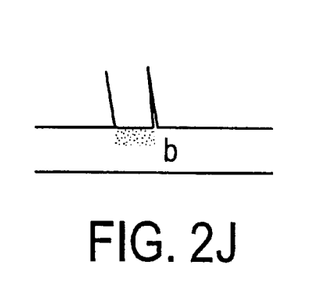

FIG. 2E illustrates the geometry and position of the stopped fluid if stopping means "a" were that of a hydrophobic restriction. FIG. 2F illustrates the geometry and position of the stopped fluid if stopping means "b" were that of a hydrophobic restriction. FIG. 2G illustrates the geometry and position of the stopped fluid if stopping means "a" were that of a hydrophilic restriction. FIG. 2H illustrates the geometry and position of the stopped fluid if stopping means "b" were that of a hydrophilic restriction. FIG. 2I illustrates the geometry and position of the stopped fluid if stopping means "a" were that of a hydrophobic patch or a film of salt. FIG. 2J illustrates the geometry and position of the stopped fluid if stopping means "b" were that of a hydrophobic patch of greater contact angle than that of "a", or a film of salt that generates a greater surface tension in the fluid than that of "a".

The example of mixing fluids as illustrated by FIGS. 2A–J is a very simple model. More complex models in which more channels are involved could be utilized to mix more than two fluids together or to mix two fluids at one timepoint and other fluids at later timepoints, e.g., by having further branches similar to channel 2 farther downstream. The fluids which are inserted into the main channel can be inserted by several means. The main channel can encompass a single port into which all fluids are inserted or it can encompass multiple ports through which fluids can be inserted. The volume of fluids inserted can be matched with the volumes of channels to yield precise filling of channels and proper mixing of the fluids.

EXAMPLE 2

Filling of Multiple Channels or Chambers with a Single Fluid

Another example of utilizing passive valves is in a network of parallel daughter channels that flow through a set of parallel wells or chambers. The goal in this case is for a fluid or sample to be evenly distributed across all channels, and for all of the wells or chambers to fill simultaneously, and for the fluid in the wells or chambers to stop in the wells or chambers and not to continue flowing into the well or chamber outlet channel until desired. Once it is desired for the fluid to continue flowing, it is desired that the fluid flow equally further down the fluid circuit, and equally into another set of chambers or wells, if present. This is performed automatically due to passive fluid dynamics. As fluid in the main channel flows toward the parallel daughter channels and wells or chambers, imperfections in the channel walls may encourage increased flow in one channel over another. The channel with increased flow will reach the well or chamber and fill up before its sister wells or chambers are filled. However, stopping means located at strategic points in the branching daughter channels will allow fluid to fill the branching channels and catch up and stop at each generation of stopping means before proceeding further down the fluid circuit. Each generation of stopping means will need to have a greater pressure barrier than the previous generation, in order to ensure the fluid does not pass one stopping means in one branch without first catching up to that generation of stopping means in all branches. In order to ensure each well or chamber is equally filled the wells or chambers are designed with stopping means at their outlets. Because it requires greater pressure for the fluid in the filled well or chamber to go through the stopping means, the increased pressure that is generated will push the fluid in the remaining channels to cause them to overcome any small wall imperfection and catch up to the fluid that is already in the well or chamber. Hence, the stopping means acts as a passive valve and allows for an even division of fluid from a single channel into several daughter channels. It also allows for a specific sample in a main channel to be evenly distributed across a network of channels. The relative structures of the stopping means will depend on the materials, the fluid, and the pressure that is required to push the fluid past any imperfections and into all the channels, wells or chambers.

Figure 3A:
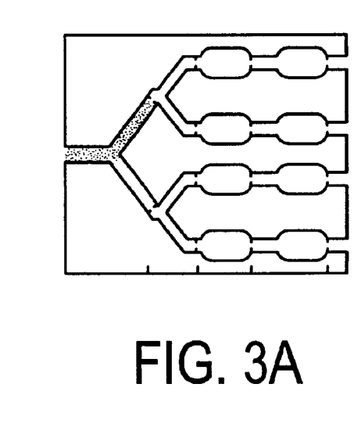
Figure 3B:
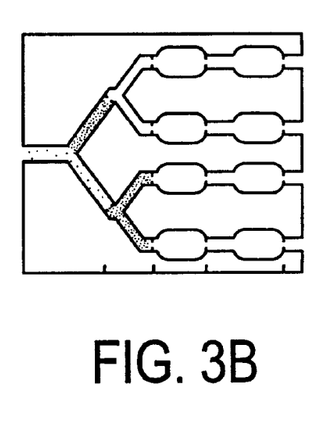
Figure 3C:
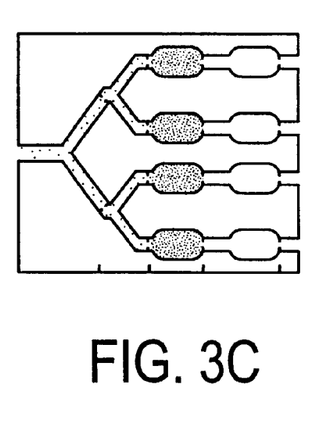
Figure 3D:
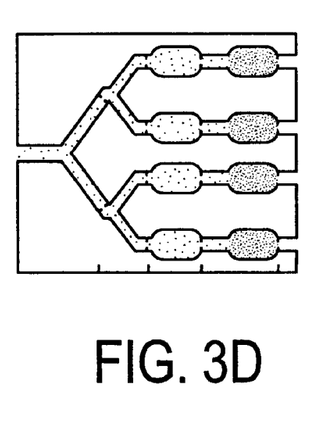
Figure 3E:
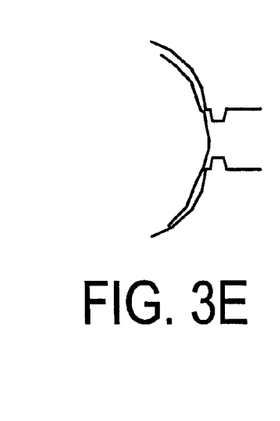
FIGS. 3E–G illustrate different configuration of the stopping means, depending on which type is being employed.
Figure 3F:
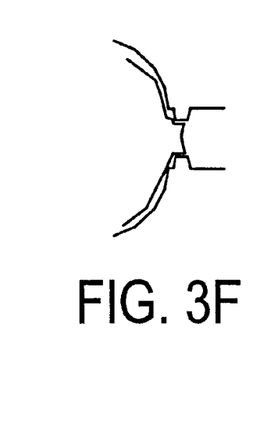
Figure 3G:
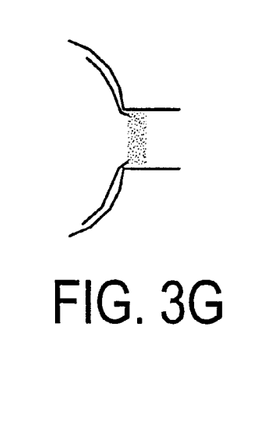

FIGS. 3A–G illustrate the effect of imperfections in microchannels and the use of stopping means to overcome problems that could have been caused by the imperfections. It also illustrates how a sample in a main channel can be evenly distributed across multiple daughter channels. In FIG. 3A fluid in one branch encounters less friction and travels further than fluid in another branch, but is stopped at the first generation of stopping means. FIG. 3B illustrates the distribution of fluid and sample as the fluid in one set of branches reach the second generation of stopping means. FIG. 3C shows that the stopping means at the outlet of the wells or chambers allow all chambers to be filled, as the back pressure generated by these stopping means causes the fluid in all the branches to push past any previous stopping means and fill the chambers equally. FIG. 3D shows that once all wells or chambers are filled, and the desired processing in the wells or chambers is completed, fluid can be pushed out of wells or chambers, through the outlet channels, and further down the fluid circuit until the next generation of stopping means are encountered. In FIGS. 3A–D the dark fluid is a sample and the lighter fluid is the system fluid. Ticks at the bottom of each figure represents the positions of the various generations of stopping means. FIG. 3E illustrates the geometry and position of the stopped fluid if the stopping means were that of a hydrophobic restriction. FIG. 3F illustrates the geometry and position of the stopped fluid if the stopping means were that of a hydrophilic restriction. FIG. 3G illustrates the geometry and position of the stopped fluid if the stopping means were that of a hydrophobic patch or a film of salt.

It is also clear to one of skill in the art that the apparatus shown in FIGS. 3A–G need not be limited to 8 wells or chambers, rather many more wells or chambers could be present. Furthermore, there is no need for the wells or chambers to all be of the same size. This makes the division of a single sample injected at point 'a' into many separate wells or chambers a very simple matter. Many reaction wells or chambers can be filled without the need for pipetting individually into each well or chamber. Rather the sample is simply inserted into the apparatus at point 'a' and the microchannels and physical forces involved result in the filling of all wells or chambers.

EXAMPLE 3

Use of an Air Duct in a Microfluidic Circuit

Another application of a stopping means is that of an air escape duct. In a hydrophobic material utilizing a narrow channel as a stopping means it takes a considerable amount of pressure to force fluid into an extremely small channel or duct (on the order of a few microns in diameter). Because of this water will easily flow by such a duct and continue down the channel it is in and not enter the duct. Air, on the other hand, will have no difficulty moving through the duct if its path in the fluid is restricted. This fact allows a method of releasing air bubbles that might be trapped within a fluid channel. A similar air escape duct can be fabricated in hydrophilic materials using a restriction and then a widening of the channel, or by utilizing a hydrophobic or salt patch.

Figure 4A:
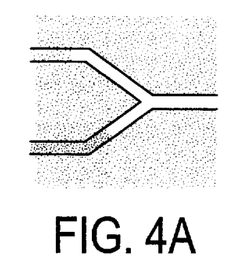
Figure 4B:
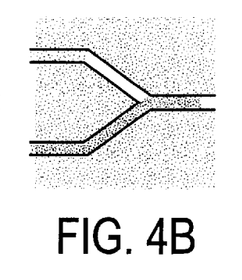
Figure 4C:
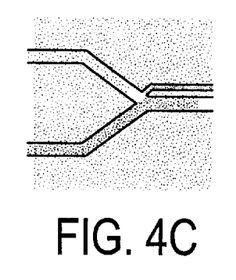
Figure 4D:
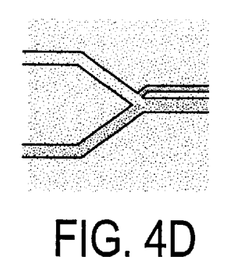
Figure 4E:
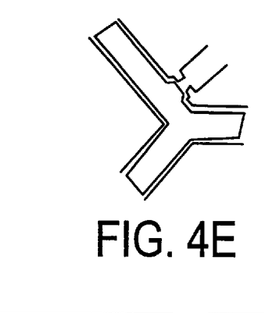
FIGS. 4E–G illustrate alternative stopping means that allow air to escape if the fluid channels are not hydrophobic.
Figure 4F:
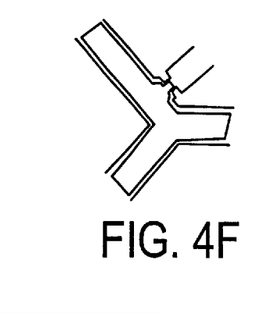
Figure 4G:
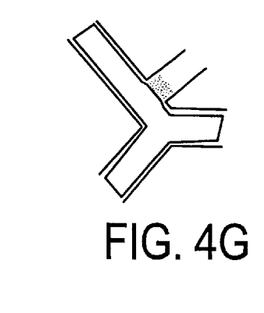

FIG. 4A shows fluid traveling down two channels that join together. FIG. 4B shows the fluid in the lower channel reaching the intersection before the fluid in the upper channel. In such an event an air bubble will trap the fluid in the upper channel and prevent the fluid in that channel from traveling further. FIG. 4C illustrates how this can be overcome by the addition of an air escape duct. In this case, fluid in the upper channel can continue to flow as the air bubble travels out of the channel into the air duct. In this illustration the air duct is represented by a long narrow channel, as might be indicative of a stopping means in a hydrophobic material. FIG. 4D illustrates fluid in both channels combining into the single channel and continuing to travel down the fluid circuit. FIG. 4E illustrates the geometry and position of the stopped fluid if the stopping means were that of a hydrophobic restriction, rather than a hydrophobic long narrow channel. FIG. 4F illustrates the geometry and position of the stopped fluid if the stopping means were that of a hydrophilic restriction. FIG. 4G illustrates the geometry and position of the stopped fluid if the stopping means were that of a hydrophobic patch or a film of salt.

Another application of an air escape duct is to allow air to escape a fluidic circuit as fluid fills the circuit. This is usually done by having air escape ducts at the endpoint in a fluid circuit, which would allow air to escape the enclosed system. This utilization of air escape ducts are depicted in FIGS. 5A–D, FIG. 6, FIGS. 8A–C, and FIGS. 10A–C which are described in greater detail in the following Examples.

EXAMPLE 4

Consolidation of Fluids

Consolidation is the case where the contents of two or more channels or wells are to be combined into a fewer number of channels or wells. An example would be when 4 separate nucleic acid sequencing reactions are performed and then it is desired to combine the 4 reactions into a single well to be run on a gel or other analytical device. Four somewhat different consolidation methods are set out in this example.

A) Two Fluid Narrow Channel Method

This method uses two fluids with a more viscous fluid being used to force a less viscous fluid through microchannels into a chamber or well to combine the less viscous fluid from multiple chambers or wells into a fewer number of chambers or wells. This method is illustrated by FIGS. 5A–D.

Figure 5A:
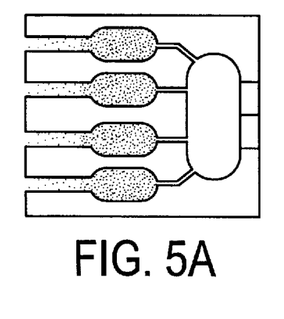
FIGS. 5A–D illustrate a two-fluid, narrow-channel method of consolidating fluid from multiple chambers into one chamber.
Figure 5B:
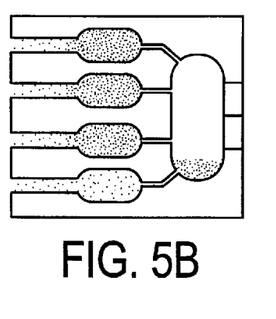
Figure 5C:
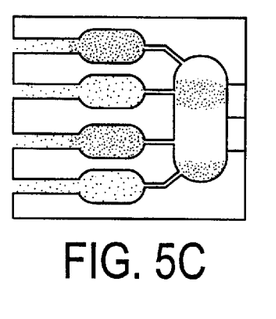
Figure 5D:
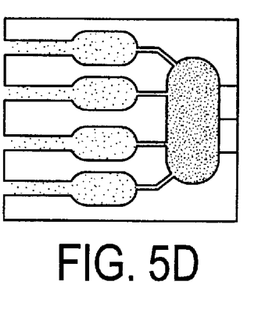

The channel or wells to be joined are filled with a fluid. The outlet of the wells or channels contain stopping means used to contain the fluid at that point in the fluid circuit. At some point upstream there is a second fluid that is more viscous than the first. There are narrow channels that connect the stopping means of the channels or wells to the point of joining. The first fluid is stopped at the stopping means (FIG. 5A). As the second viscous fluid advances down a channel it will force the first fluid through the stopping means into the narrow channel and into the point of joining or consolidation chamber (FIG. 5B). When the second fluid reaches the stopping means it does not stop because the fluid meniscus is gone. However, the pressure required to force the more viscous solution through the narrow channel is instead used to push the first fluid in a neighboring channel into the point of joining (FIG. 5C). This process is repeated until all wells or channels are emptied of the first fluid and the pumping is stopped (FIG. 5D). FIGS. 3E–G illustrate the possible geometries and positions of the stopped fluid if the stopping means at the outlet of the channels or wells were that of a hydrophobic restriction, a hydrophilic restriction, or a hydrophobic patch or salt film, respectively. If the material were hydrophobic, only a long narrow channel would be needed, rather than both a restriction and then a long narrow channel. The utilization of air escape ducts at the consolidation chamber would be similar to those depicted in Example 3 and FIGS. 4E–G.

Figure 6:
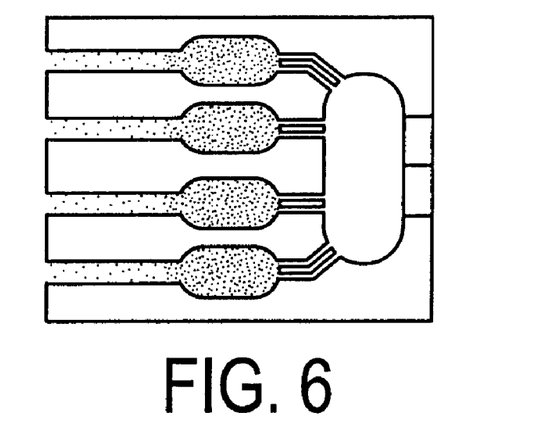
FIG. 6 illustrates a two-fluid, narrow-channel method of consolidating fluid from multiple chambers into one chamber wherein multiple narrow connecting channels connect the stopping means of each of the multiple chambers to the consolidation chamber.

Since the narrow connecting channels are very small there is a high chance of them becoming occluded by small particles. To reduce this risk redundant channels may be made. This is illustrated by FIG. 6. This will help ensure the likelihood of an open channel being present to allow proper consolidation.

B) Joining Channel with Restriction and Air Escape Vent Method

Figure 7A:
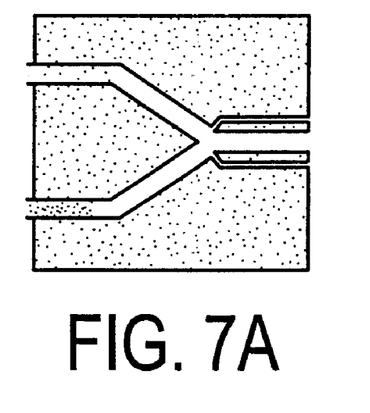
FIGS. 7A–D illustrate the concept of using air escape vents in conjunction with each of two channels wherein each of the channels comprises a stopping means.
Figure 7B:
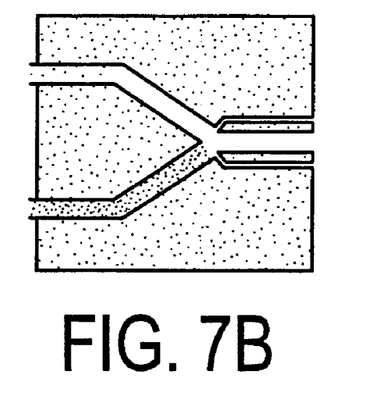
Figure 7C:
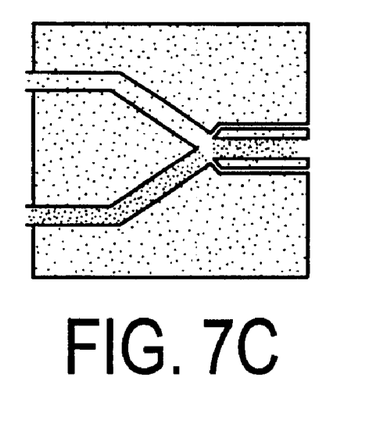
Figure 7D:
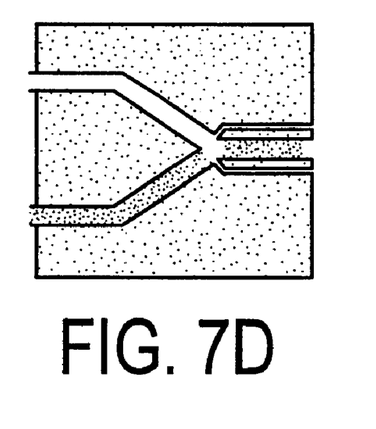

The concept of having an air escape vent present to allow the release of what normally would be a trapped bubble is discussed above in Example 3. A variation is shown here in a method of consolidation wherein stopping means are present (see FIGS. 7A–D). FIG. 7A shows two fluids each entering a channel. Each channel has a stopping means at the point where the two channels on the left join to become a single channel. This allows the fluid in both channels to catch up to themselves at the point where the channels join (FIG. 7C). The presence of an air vent in each of the two initial channels ensures that neither channel will have an air lock and both will advance to the joining region. Once one fluid breaks through its stopping means it will wet the other surface of the stopping means in the neighboring channel, eliminating its meniscus. This will allow both fluids to flow into the joining channel and mix together (FIG. 7D). Structure and position of fluid in the stopping means and air escape ducts have been shown in FIGS. 2E–J and 4 E–G.

C) Air Displacement Method

Another method of consolidation requires the use of ports coming from a third dimension, e.g., from above or below.

Figure 8A:
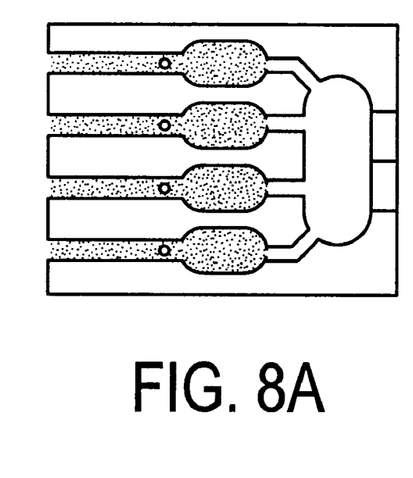
FIGS. 8A–C illustrate the use of ports to allow the introduction of air, another gas, or a second fluid to be introduced to force fluids past a stopping means.
Figure 8B:
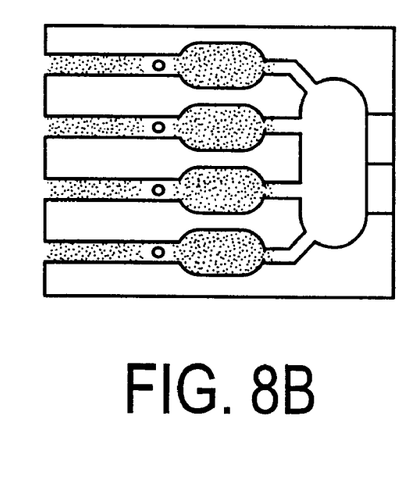
Figure 8C:
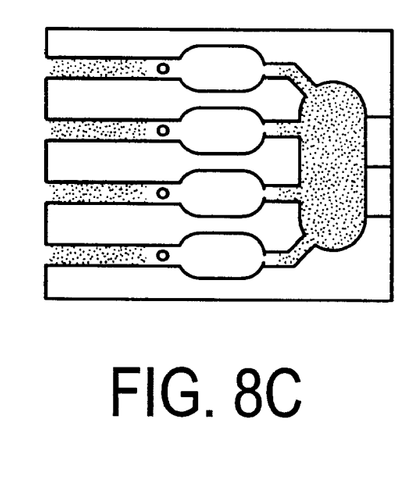

The ports possess stopping means at their connection point to the fluid channel so that, under normal operating pressures, fluid will not flow into them. Fluid flows into wells or channels and is stopped at a known location due to the use of stopping means (FIG. 8A, stopping means exist at the right of each of the 4 initial wells between each well and the exiting microchannel). Air or another gas is pushed through the ports (appearing as holes to the left of the 4 initial wells in FIGS. 8A–C) into the fluid channels. The air will displace the fluid downstream past the stopping means (FIG. 8B), and in this case, into the consolidation well (FIG. 8C). Air escape ducts in the consolidation well allow displaced air to exit the system, so fluid can fill the consolidation well. A second fluid, rather than air, could also be pushed through the ports and used to displace the well volumes into the consolidation chamber.

D) Physical Displacement Method

Figure 9A:
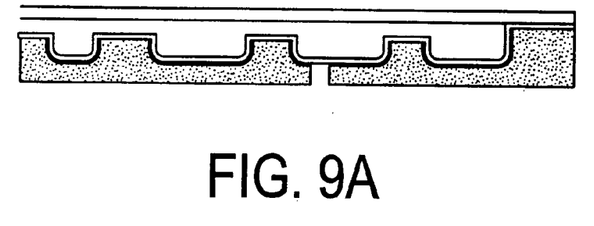
FIGS. 9A–D illustrate a physical displacement method in which pressure is applied to a flexible region of a circuit thereby forcing the fluid in the circuit to be moved.
Figure 9B:
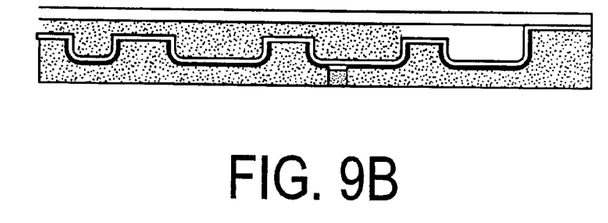
Figure 9C:
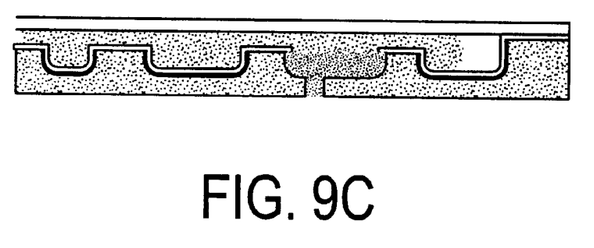
Figure 9D:
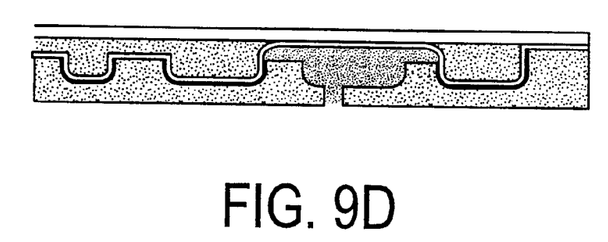

This method also requires the use of a third dimension. In this case a portion, preferably the top or bottom, of the fluid circuit is made to be flexible at the point where physical displacement is to occur. The top or bottom plate has an opening that can allow a displacement means to compress the flexible fluid circuit to push fluid further downstream. This displacement means can be a fluid such as water, a gas such as air, or a plunger of some kind. This is illustrated in FIGS. 9A–D. FIG. 9A shows an empty circuit. FIG. 9B shows the circuit Ad partially filled with fluid. The bottom of the wells is made of a flexible material. In this example, a displacement means (water) is introduced below the last well filled with fluid. The water compresses the bottom of the well (FIG. 9C) forcing the fluid from the well into the neighboring empty well (FIG. 9D). The displacement means can be introduced elsewhere and need not be directly at the last filled well.

EXAMPLE 5

Modified Two Fluid Narrow Channel Methods of Consolidation

Figure 10A:
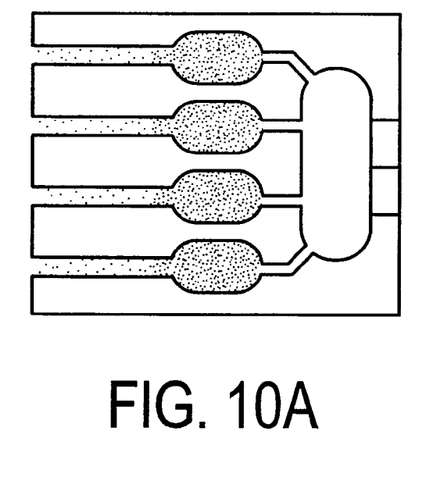
FIGS. 10A–C illustrate three versions of a consolidation circuit.
Figure 10B:
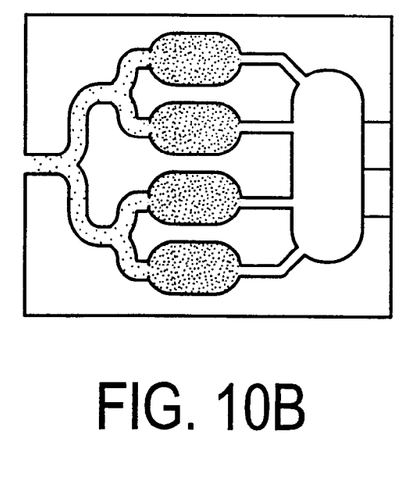
Figure 10C:
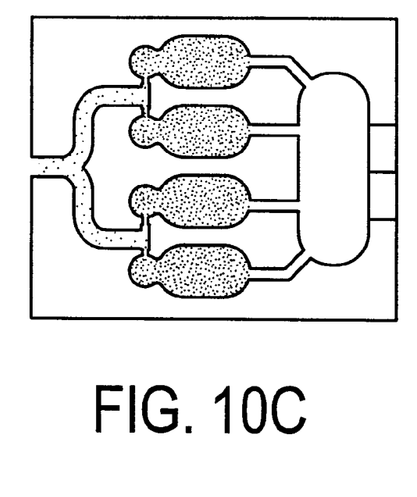

The method described above in Example 4, Section A, and illustrated in FIGS. 5A–D has been modified to yield improved results. Two modifications are illustrated in FIGS. 10B–C with FIG. 10A showing the original design for comparison. The design shown in FIG. 10B incorporates stopping means just upstream of each of the four wells. These stopping means facilitate an even distribution of a sample into each of the channel branches leading to the four wells. Although not illustrated in FIGS. 5A or 10A, the 4 channels leading to the wells could have branched off from a single source or alternatively could have come from 4 different sources.

In practice the design of FIG. 10B does not work very well. This is because hydrophobic or hydrophilic restrictions act as jet nozzles pushing the second, more viscous fluid into the first fluid and causing unwanted mixing. This results in consolidation that is less than optimum and a fair amount of the second solution is found in the large consolidation well at the right in FIG. 10B. Although this is useful as a mixing method, it is not the desired result in this case.

FIG. 10C illustrates a modification of the consolidation design that eliminates the unwanted mixing seen with the design shown in FIG. 10B. The entrance channel is put on the side of the well and the well is shaped somewhat in the form of a bowling pin where one bulb or section is significantly larger than the other section and the channel joining the two is not necessarily narrow and sharp. This allows the velocity of the second fluid to slow down and stabilize in the small first section before it interacts with the bulk of the first fluid in the large second section. If the transition between the first and second sections is smooth and gradual the second fluid (if properly chosen) will remain intact with itself and there will be a clear division between the first and second fluids as the second fluid fills the well and forces the first fluid through the narrow channel into the consolidation well.

EXAMPLE 6

Temporarily Bypassing a Fluid Circuit Section

Example 1 illustrated the use of stopping means to divert fluid from one path to a branching path of a microfluidic circuit. Example 3 illustrated the use of air escape ducts to allow what would normally be trapped air to escape a channel and allow fluid to flow through the channel, and eventually combine with the fluid in a joining channel. Utilizing these techniques a fluid circuit section can be temporarily bypassed using stopping means that divert fluid into a different path. A downstream stopping means can be used to overcome the pressure barrier at the original stopping means, and then an air escape duct can be used to allow fluid to flow through the bypassed region and rejoin the fluid circuit from which it had been cut off.

Figure 11A:
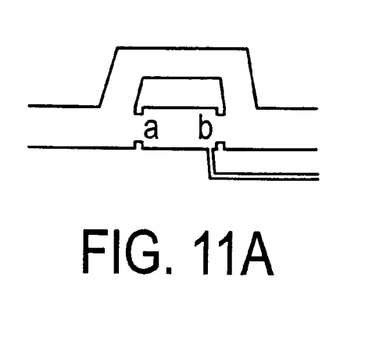
FIGS. 11A–E illustrate the combination of stopping means and air escape vents to allow fluid to bypass a particular fluid circuit section. The bypassed region can be later perfused by a downstream stopping means generating enough backpressure to overcome the original stopping means that prevented flow into the non-perfused region.
Figure 11B:
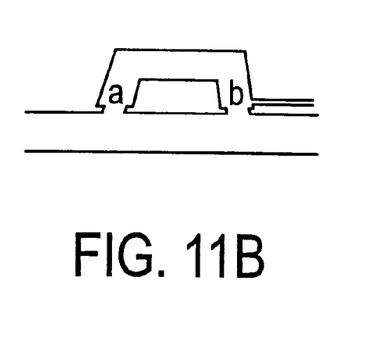
Figure 11C:
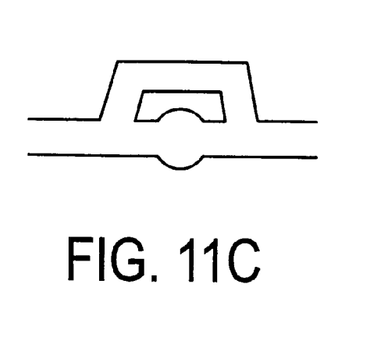
Figure 11D:
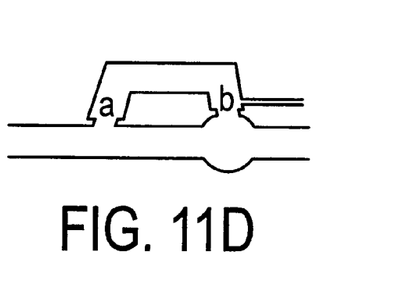
Figure 11E:
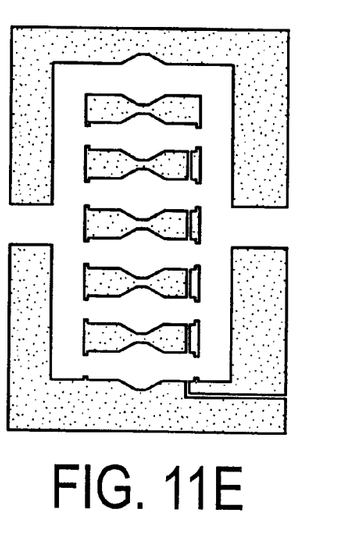

FIGS. 11A–E illustrate this technique. In FIG. 11A fluid flows down a main channel and encounters a stopping means "a" that diverts the flow into a side channel. When the side channel rejoins the main channel it is prevented from entering the bypassed region of the main channel because of a second stopping means "b" that diverts the fluid to flow further down the main channel. At some point downstream another stopping means with a greater pressure barrier than the original stopping means "a" causes fluid to push past stopping means "a". An air escape duct located at the upstream side of stopping means "b" allows fluid to flow through the main channel. When it reaches stopping means "b" the meniscus disappears and the pressure barrier at stopping means "b" is eliminated. Fluid can then flow through both the main channel and side channel according to their respective impedances. It is important that the pressure barrier at stopping means "b" is greater than the pressure barrier at stopping means "a" to ensure fluid does not push past stopping means "b" before it pushes past stopping means "a". FIG. 11B illustrates a similar situation, except where fluid in a main channel is prevented from entering a side channel due to stopping means at "a" and "b". FIG. 11C illustrates a chamber or well in the fluid circuit that may be bypassed initially, or perfused initially, depending on the location of the stopping means and air escape ducts. FIG. 11D illustrates a chamber that is located at the point of joining of two channels, where one inlet to the chamber is a bypassed branch from the main channel. FIG. 11E illustrates a main channel that includes a chamber, and a series of secondary channels that contain chambers and that are bypassed, all of which contain stopping means to prevent their perfusion, and air escape ducts that allow their ultimate perfusion. The stopping means at the upstream positions of the secondary channels are designed such that their pressure barriers can be overcome in the sequence that is desired, in this illustration from the top to the bottom, for the fluid circuit to function properly. The air escape ducts can either sequentially lead to the secondary channels that are not yet perfused, or can lead to the outside via ducts traveling in a third dimension.

The above examples demonstrate methods of diluting or mixing two fluids traveling beside one another in a single channel, methods of allowing branching channels to divide flowing fluid, methods of allowing air to escape out of a fluid circuit, methods of consolidating channels or samples, and methods of temporarily bypassing a fluid path, all using passive fluid dynamics based on pressure barriers created by manipulating fluid capillary forces.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

List of References

U.S. Pat. No. 4,946,795
U.S. Pat. No. 5,119,116
U.S. Pat. No. 5,498,392
U.S. Pat. No. 5,587,128
U.S. Pat. No. 5,627,041
U.S. Pat. No. 5,726,026
R. C. Anderson et al., "Microfluidic biochemical analysis system, " Int. Conf. On Solid-State Sens and Act, Transducers '97, p477–80 (1997).
S. N. Brahmasandra et al., "A microfabricated fluidic reaction and separation system for integrated DNA analysis," *Micro Total Analysis Systems* '98, D. J. Harrison and A Van den Berg, eds., p267–70, Kluwer Acad. Publ. Dordrecht (1998).
K. Hosokawa et al., "Hydrophobic microcapillary vent for pneumatic manipulation of liquid in μTAS, " *Micro Total Analysis Systems* '98, D. J. Harrison and Van den Berg, eds., p307–10, Kluwer Acad. Publ. Dordrecht (1998).
P. F. Man et al., "Microfabricated capillarity-driven stop valve and sample injector," IEEE 11$^{th}$ Annual Int. MEMS Workshop, p45–50 (1998).

What is claimed is:

1. A non-wetted fluid circuit useful for consolidating or mixing fluids, said fluid circuit comprising a first microchannel and a second microchannel joining at an intersection to form a common downstream microchannel, wherein said first microchannel comprises a passive stopping means immediately upstream from said intersection; wherein said passive stopping means creates resistance to an advancing first fluid to temporarily block the flow of said first fluid in said first microchannel prior to wetting of the downstream side of said passive stopping means, and permits flow of said first fluid through said passive stopping means upon wetting of the downstream side of said passive stopping means by a second fluid entering said intersection from said second microchannel, wherein said passive stopping means comprises a local modification to the dimensions or surface properties of said first microchannel selected from the group consisting of a hydrophobic patch, a surface tension patch, a hydrophobic short channel narrowing, a hydrophilic short channel narrowing, and a hydrophilic channel widening, and wherein said passive stopping means is sufficient to at least temporarily block the flow of fluid in said first microchannel.

2. The fluid circuit of claim 1, wherein said first fluid and said second fluid have substantially the same surface energies.

3. The fluid circuit of claim 1, wherein said passive stopping means is created by an abrupt change in the capillary force experienced by fluid flowing in said first microchannel.

4. The fluid circuit of claim 1, wherein said passive stopping means is created by a change in at least one of the contact angle between said first fluid and said first microchannel and the diameter of said first microchannel.

5. The fluid circuit of claim 1, wherein said passive stopping means is selected from the group consisting of a hydrophobic short channel narrowing, a hydrophilic short channel narrowing, a hydrophilic channel widening, a hydrophobic patch, and a surface tension patch.

6. The fluid circuit of claim 1, wherein at least a portion of the interior of said fluid circuit comprises a hydrophobic material.

7. The fluid circuit of claim 6, wherein said hydrophobic material is selected from the group consisting of polytetrafluoroethylene, fluorinated ethylenepropylene, perfluoralkoxy alkane, and polyvinylidene fluoride.

8. The fluid circuit of claim 1, wherein at least a portion of the interior of said fluid circuit comprises a hydrophilic material.

9. The fluid circuit of claim 8, wherein said hydrophilic material is elastophilic™.

10. The fluid circuit of claim 1 wherein at least one of said first microchannel and said second microchannel comprises a vent upstream of said intersection.

11. The fluid circuit of claim 10 wherein said vent allows the passage of gaseous materials but not fluids.

12. A fluid circuit comprising:
    a parent microchannel having an upstream end and a downstream end;
    at least two daughter microchannels branching from said downstream end of said parent microchannel, each said daughter microchannel having an upstream end and a downstream end;
    a first passive pressure barrier sufficient to at least temporarily block fluid advancing from said parent microchannel to one said daughter microchannel; and
    a second passive pressure barrier sufficient to at least temporarily block fluid advancing out of one said daughter microchannel in a downstream direction;
    wherein said second passive pressure barrier provides a greater resistance to advancing fluid than does said first passive pressure barrier.

13. The fluid circuit of claim 12, wherein said first pressure barrier is created by an abrupt change in the capillary force experienced by fluid at said first pressure barrier, and said second pressure barrier is created by an abrupt change in the capillary force experienced by fluid at said second pressure barrier.

14. The fluid circuit of claim 12, wherein said first pressure barrier is created by an abrupt change microchannel diameter at the junction said parent microchannel and said one daughter microchannel.

15. The fluid circuit of claim 12, wherein at least one of said first pressure barrier and said second pressure barrier is selected from the group consisting of a hydrophobic short channel narrowing, a hydrophilic short channel narrowing, a hydrophilic channel widening, a hydrophobic patch, and a surface tension patch.

16. A fluid circuit comprising:
    a parent microchannel having an upstream end mid a downstream end;
    at least two first generation daughter microchannels branching from said downstream end of said parent microchannel, each said first generation daughter microchannel having an upstream end and a downstream end;
    at least two second generation daughter microchannels branching from the downstream end of at least one said first generation daughter microchannel;
    at least a first passive pressure barrier sufficient to at least temporarily block fluid advancing out of one said first generation daughter microchannels in a downstream direction prior to wetting of a downstream side of said first pressure baffler; and at least a second passive pressure barrier sufficient to at least temporarily block fluid advancing out of one said second generation daughter microchannels in a downstream direction prior to wetting of a downstream side of said second pressure barrier;

wherein said second passive pressure barrier provides a greater resistance to advancing fluid than does said first passive pressure barrier.

17. The fluid circuit of claim 16, further comprising at least one well or chamber connected downstream of at least one said second generation daughter microchannel.

18. The fluid circuit of claim 16, wherein said first pressure barrier is created by an abrupt change in the capillary force experienced by fluid at said first pressure barrier, and said second pressure barrier is created by an abrupt change in the capillary force experienced by fluid at said second pressure barrier.

19. The fluid circuit of claim 16 wherein said first pressure barrier is created by an abrupt change in microchannel diameter at the junction said one first generation daughter channel and one said second generation daughter microchannel.

20. The fluid circuit of claim 16, wherein at least one of said first pressure barrier and said second pressure barrier is selected from the group consisting of a hydrophobic short channel narrowing, a hydrophilic short channel narrowing, a hydrophilic channel widening, a hydrophobic patch, and a surface tension patch.

21. A non-wetted fluid circuit having an hydrophobic inner surface and comprising a plurality of connected microchannels, wherein at least one said microchannel comprises a short microchannel narrowing, said microchannel narrowing having an inlet, an outlet, and a cross-sectional configuration relative to the microchannel tat creates a passive pressure barrier sufficient to temporarily block the flow of fluid that is advancing through said fluid circuit prior to wetting of a downstream side of said narrowing and to cause the fluid preferably to flow in an adjoining microchannel connected upstream of said narrowing rather to flow past said narrowing.

22. The fluid circuit of claim 21, wherein said fluid circuit is formed in a hydrophobic material.

23. The fluid circuit of claim 22, wherein said hydrophobic material comprises one or more materials selected from the group consisting of polytetrafluoroethylene, fluorinated ethylenepropylene, perfluoralkoxy alkane, and polyvinylidene fluoride.

24. The fluid circuit of claim 21, wherein the inner surface of said fluid circuit comprises a hydrophobic coating.

25. The fluid circuit of claim 24, wherein said hydrophobic coating comprises one or more materials selected from the group consisting of polytetrafluoroethylene, fluorinated ethylenepropylene, perfluoralkoxy alkane, and polyvinylidene fluoride.

26. A non-wetted fluid circuit having an hydrophilic inner surface and comprising a plurality of connected microchannels, wherein at least one said microchannel comprises a short microchannel narrowing, said microchannel narrowing having an inlet, an outlet, and a cross-sectional configuration relative to the microchannel that creates a passive pressure barrier sufficient to temporarily block the flow of fluid that is advancing through said fluid circuit prior to wetting of a downstream side of said narrowing and to cause the fluid preferably to flow in an adjoining microchannel connected upstream or said narrowing rather than to flow past said narrowing.

27. The fluid circuit of claim 26, wherein said fluid circuit is formed in a hydrophilic material.

28. The fluid circuit of claim 37, wherein said hydrophilic material comprises one or more materials selected from the group consisting of metal, glass, PMMA, polycarbonate, nylon 6/12 and PVC.

29. The fluid circuit of claim 26, wherein the inner surface of said fluid circuit comprises a hydrophilic coating.

30. The fluid circuit of claim 29, wherein said hydrophilic coating is elastophilic™.

31. A non-wetted fluid circuit comprising a plurality of connected microchannels, wherein at least one said microchannel comprises a passive pressure barrier sufficient to temporarily block the flow fluid that is advancing through said fluid circuit prior to wetting of a downstream side of said passive pressure barrier and to cause the fluid preferably to flow in an adjoining microchannel connected upstream of said passive pressure baffler rather than flowing through said passive pressure barrier, wherein said passive pressure baffler comprises a local modification to the dimensions or surface properties of said at least one microchannel selected from the group consisting of a hydrophobic patch, a surface tension patch, a hydrophobic short channel narrowing, a hydrophilic short channel narrowing, and a hydrophilic channel widening to, and wherein said passive pressure barrier is sufficient to at least temporarily block the flow of fluid in said at least one microchannel.

32. The fluid circuit of claim 31, further comprising a coating on at least a portion of said fluid circuit.

33. The fluid circuit of claim 32, wherein said coating comprises a hydrophobic material.

34. The fluid circuit of claim 33, wherein said hydrophobic material is selected from the group consisting of polytetrafluoroethylene, fluorinated ethylenepropylene, perfluoralkoxy alkane, and polyvinylidene fluoride.

35. The fluid circuit of claim 32, wherein said coating comprises a hydrophilic material.

36. The fluid circuit of claim 35, wherein said hydrophilic material is elastophilic™.

37. A fluid circuit comprising at least a first microchannel and a second microchannel, said second microchannel joining said first microchannel at an intersection, said first microchannel comprising a passive stopping means downstream of said intersection, said passive stopping means causing fluid which is advancing through said fluid circuit preferably to flow in said second microchannel rather than to flow past said passive stopping means, wherein said passive stopping means is created by an abrupt change in the capillary force experienced by fluid advancing in said first microchannel, wherein said passive stopping means comprises a local modification to the dimensions or surface properties of said first microchannel selected from the group consisting of a hydrophobic patch, a surface tension patch, a hydrophobic short channel narrowing, a hydrophilic short channel narrowing, and a hydrophilic channel widening to, and wherein said passive stopping means is sufficient to at least temporarily block the flow of fluid in said first microchannel.

38. The fluid circuit of claim 37, wherein said passive stopping means is created by a change in at least one of the contact angle between said fluid and said first microchannel and the diameter of said first microchannel.

39. A method of controlling fluid flow through a non-wetted fluid circuit comprising at least two connected microchannels, each said microchannel containing a passive fluid flow barrier that creates a fluid pressure barrier, said method comprising:

advancing fluid in a first microchannel until it is stopped by the fluid engaging a first passive fluid flow barrier;

advancing fluid in a connected neighboring second microchannel until it reaches a second passive fluid flow barrier; and overcoming the pressure barrier of one of said first and second passive fluid flow barriers by the fluid engaging the other of said first and second passive fluid flow barriers and with the application of sufficient pressure to the fluid;

wherein each of said first and second passive fluid flow barriers comprises a local modification to the dimensions or surface properties of the microchannel in which it is located selected from the group consisting of a hydrophobic patch, a surface tension patch, a hydrophobic short channel narrowing, a hydrophilic short channel narrowing, and a hydrophilic channel widening, wherein said first and second passive fluid flow barriers are sufficient to at least temporarily block the advancing flow of fluid in the microchannel; and wherein one of said first and second passive fluid flow barriers creates a weaker pressure barrier than the other said passive fluid flow barrier, and wherein said weaker barrier is overcome first.

40. The method of claim 39, wherein fluid is directed into a connected neighboring second microchannel as a consequence of said fluid engaging said first passive fluid flow barrier in said first microchannel.

* * * * *